US010088426B2

United States Patent
Wang et al.

(10) Patent No.: US 10,088,426 B2
(45) Date of Patent: Oct. 2, 2018

(54) CHEMILUMINESCENCE IMAGING SYSTEM AND METHOD OF MONITORING A COMBUSTOR FLAME OF A TURBINE ENGINE

(71) Applicant: United Technologies Corporation, Hartford, CT (US)

(72) Inventors: Hongcheng Wang, Farmington, CT (US); Jeffrey M. Cohen, Hebron, CT (US)

(73) Assignee: United Technologies Corporation, Farmington, CT (US)

( * ) Notice: Subject to any disclaimer, the term of this patent is extended or adjusted under 35 U.S.C. 154(b) by 398 days.

(21) Appl. No.: 14/704,599

(22) Filed: May 5, 2015

(65) Prior Publication Data
US 2015/0323467 A1    Nov. 12, 2015

Related U.S. Application Data

(60) Provisional application No. 61/989,303, filed on May 6, 2014.

(51) Int. Cl.
G01N 21/25    (2006.01)
G01N 21/76    (2006.01)
G01N 21/64    (2006.01)

(52) U.S. Cl.
CPC ....... *G01N 21/766* (2013.01); *G01N 21/6428* (2013.01); *G01N 2021/6484* (2013.01); *G01N 2201/12* (2013.01)

(58) Field of Classification Search
CPC ............. G01N 21/645; G01N 21/6428; G01N 21/6452; G01N 2021/6421; G01N 2021/6484

USPC ......................................................... 356/417
See application file for complete search history.

(56) References Cited

U.S. PATENT DOCUMENTS

| 8,203,714 B2 | 6/2012 | Merklein | |
|---|---|---|---|
| 2005/0134959 A1* | 6/2005 | Simpson | B32B 17/10 359/359 |
| 2010/0103424 A1* | 4/2010 | Davis, Jr. | F23N 5/082 356/402 |
| 2010/0201988 A1* | 8/2010 | Kiesel | G01N 21/05 356/419 |

(Continued)

OTHER PUBLICATIONS

Michael Schoberl, "Evaluation of a High Dynamic Range Video Camera with Non-Regular Sensor", Digital Photography IX, Proc. of SPIE-IS&% Electronic Imaging, SPIE vol. 8660, 86600M, doi: 10.1117/12.2004258, 2013.

(Continued)

*Primary Examiner* — Md M Rahman
(74) *Attorney, Agent, or Firm* — O'Shea Getz P.C.

(57) ABSTRACT

A chemiluminescence imaging system that may be used for monitoring a combustor flame of a gas turbine engine includes a sensor array having a plurality of pixels operable to capture an image. A multispectral mask array and an attenuation filer array of the system may be generally placed in front of the sensor array and each have a plurality of cells that are generally align, respectively, to the plurality of pixels. Each cell is generally one of a plurality of band-pass filter types distributed randomly across the multispectral mask array and an image reconstruction algorithm is used to produce at least one image for evaluating properties of the flame.

13 Claims, 3 Drawing Sheets

(56) References Cited

U.S. PATENT DOCUMENTS

| | | | |
|---|---|---|---|
| 2011/0008737 A1* | 1/2011 | McManus | F23N 1/022 |
| | | | 431/12 |
| 2012/0280134 A1 | 11/2012 | Diebold | |
| 2015/0208005 A1 | 7/2015 | Moesle | |
| 2015/0215529 A1* | 7/2015 | Wang | G06T 5/007 |
| | | | 348/218.1 |
| 2015/0219809 A1 | 8/2015 | Ruhnau | |

OTHER PUBLICATIONS

Cyrus B. Meher-Homji, "Gas Turbine Fuels—System Design, Combustion and Operability", Proceedings of the 39th Turbomachinery Symposium, pp. 155-186, 2010.

Yolanda R. Hicks, "Optical Measurement and Visualization in High-Pressure, High-Temperature, Aviation Gas Turbine Combustors", NASA/TM—2000-210377, Sep. 2000.

Christoph Knappe, "Phosphor Thermometry on Surfaces a Study of its Methodology and its Practical Applications", Division of Combustion Physics Department of Physics Lund University, 2013.

T.M. Muruganandam, "Chemiluminescence Based Sensors for Turbine Engines", 39th AIAA/ASME/SAE/ASEE Joint Propulsion Conference & Exhibit, AIAA 2003-4490, Huntsville, Alabama, Jul. 20-23, 2003.

Ronald Whiddon, "Application of Laser-based Diagnostics to a Prototype Gas Turbine Burner at Selected Pressures", Lund University, Apr. 2014.

\* cited by examiner

CHEMILUMINESCENCE IMAGING SYSTEM AND METHOD OF MONITORING A COMBUSTOR FLAME OF A TURBINE ENGINE

This application claims priority to U.S. Patent Appln. No. 61/989,303 filed May 6, 2014.

BACKGROUND

The present application relates to an imaging system and more particularly to a chemiluminescence imaging system for monitoring a combustor flame of a turbine engine and method of monitoring.

Two dimensional spectral imaging of combustor flame emission, measures chemiluminescence over a spatial area. Known systems require multiple CCD or CMOS cameras each equipped with band-pass filters to image the electronically excited methylidyne radical (CH*) and electronically excited dicarbon radicals (C2*) emission occurring throughout the flame. The known systems require complex optical designs and calibration resulting in a large system footprint (i.e. bulky) and high costs to procure and maintain.

SUMMARY

A chemiluminescence imaging system according to one, non-limiting, embodiment of the present disclosure includes a sensor array including a plurality of pixels operable to capture an image; a multispectral mask array having a plurality of cells with each cell associated with a respective pixel and being one of a plurality of band-pass filter types with the plurality of band-pass filter types being distributed across the multispectral mask; and an attenuation filter array adjacent to the multispectral mask array and having a plurality of cells with each cell associated with a respective cell of the multispectral mask array for obtaining proper exposure of each of the plurality of pixels.

Additionally to the foregoing embodiment, the system includes a computer having an image reconstruction algorithm.

In the alternative or additionally thereto, in the foregoing embodiment, the plurality of band-pass filter types are randomly distributed.

In the alternative or additionally thereto, in the foregoing embodiment, the sensor array is a charge coupled device.

In the alternative or additionally thereto, in the foregoing embodiment, the system has only one sensor array that is part of a camera.

In the alternative or additionally thereto, in the foregoing embodiment, each one of the plurality of band-pass filter types are configured to measure a distinct wavelength range of spectral light of a turbine combustor flame.

In the alternative or additionally thereto, in the foregoing embodiment, a first band-pass filter type of the plurality of band-pass filter types passes light emissions within a wavelength range of about 503 nm to 519 nm associated with an electronically excited dicarbon radical, and a second band-pass filter type passes light emissions within a wavelength range of about 422 nm to 432 nm associated with an electronically excited methylidyne radical.

In the alternative or additionally thereto, in the foregoing embodiment, the third band-pass filter is a wide-band filter and passes light emissions within wavelength ranges of about 442 nm to 459 nm, 520 nm to 539 nm, and 600 nm to 617 nm.

In the alternative or additionally thereto, in the foregoing embodiment, the system has only one sensor array that is part of a camera.

In the alternative or additionally thereto, in the foregoing embodiment, the attenuation filter array is a plurality of attenuation films adhered to the multispectral mask array.

In the alternative or additionally thereto, in the foregoing embodiment, the attenuation filter array is orientated behind the multispectral mask array.

In the alternative or additionally thereto, in the foregoing embodiment, the attenuation filter array is orientated in front of the multispectral mask array.

In the alternative or additionally thereto, in the foregoing embodiment, the sensor array is a CMOS.

A gas turbine combustor imaging system according to a second, non-limiting, embodiment includes a single sensor array including a plurality of pixels operable to capture an image; a multispectral mask array including a plurality of cells with each cell associated with a respective pixel, and with each cell being one of a plurality of band-pass filter types pseudo-randomly distributed across the multispectral mask array, and each one of the plurality of band-pass filter types being configured to measure a distinct wavelength range of spectral light of a turbine combustor flame; and a computer communicating with the sensor array and provided with an image reconstruction algorithm for reconstructing the image.

Additionally to the foregoing embodiment, the system includes an attenuation filter array orientated adjacent to the multispectral mask array for obtaining proper exposure of each of the plurality of pixels.

In the alternative or additionally thereto, in the foregoing embodiment, a first band-pass filter type of the plurality of band-pass filter types passes light emissions within a wavelength range of about 503 nm to 519 nm associated with an electronically excited dicarbon radical, and a second band-pass filter type passes light emissions within a wavelength range of about 422 nm to 432 nm associated with an electronically excited methylidyne radical.

In the alternative or additionally thereto, in the foregoing embodiment, a third band-pass filter type of the plurality of band-pass filter types is a wide-band filter and passes light emissions within wavelength ranges of about 442 nm to 459 nm, 520 nm to 539 nm, and 600 nm to 617 nm generally associated with background radiation.

In the alternative or additionally thereto, in the foregoing embodiment, the image reconstruction algorithm utilizes Dictionary Learning.

In the alternative or additionally thereto, in the foregoing embodiment, the attenuation filter array is orientated behind the multispectral mask array.

A method of monitoring a combustor flame of a gas turbine engine according to another, non-limiting, embodiment includes the steps of taking a chemiluminescence image of the combustor flame utilizing a single sensor array including a plurality of pixels operable to capture the image, and a multispectral mask array having a plurality of cells with each cell associated with a respective pixel, and with each cell being one of a plurality of band-pass filter types pseudo-randomly distributed across the multispectral mask array, and each one of the plurality of band-pass filter types being configured to measure a distinct wavelength range of spectral light of a turbine combustor flame; reconstructing the image utilizing an image reconstruction algorithm; evaluating the spatial distribution of heat release from the reconstructed image that portrays electronically excited methylidyne radicals and hydroxide radicals; and evaluating the spatial distribution of fuel-to-air ratios from the reconstructed image that portrays electronically excited dicarbon radicals and the methylidyne radicals.

The foregoing features and elements may be combined in various combination without exclusivity, unless expressly indicated otherwise. These features and elements as well as the operation thereof will become more apparent in light of the following description and the accompanying drawings. It should be understood, however, the following description and figures are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
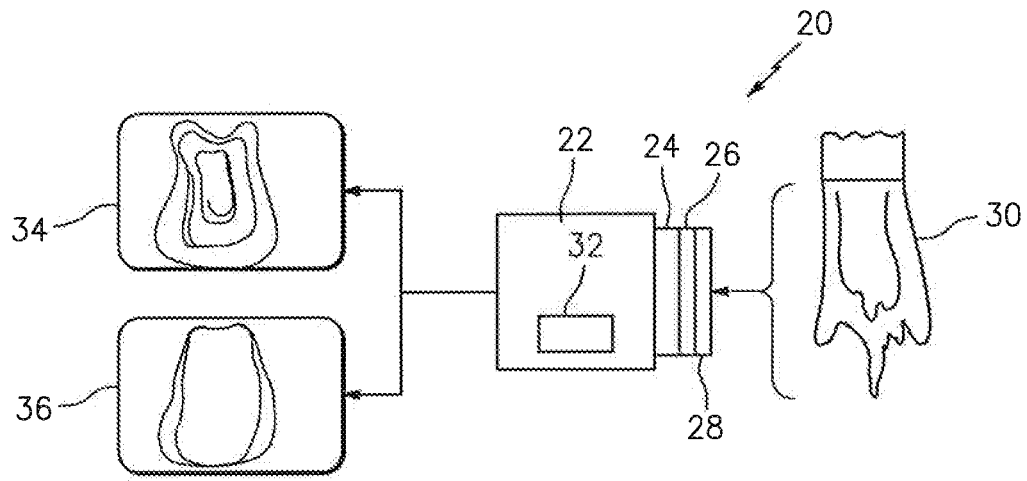
FIG. 1 is a schematic of a chemiluminescence imaging system of the present disclosure.

Referring to FIG. 1, a chemiluminescence imaging system 20 according to one, non-limiting embodiment of the present disclosure is illustrated. System 20 may include a computer or processor 22, a camera or sensor array 24, a multispectral mask array 26 and an attenuation filter array 28, and may be constructed to monitor and image a combustor flame 30 of a gas turbine engine as one example. After the sensor array 24 images the flame 30, the computer 22 applies an image reconstruction algorithm 32 to construct a first output or heat image 34 that displays a spatial distribution of heat release from the flame 30, and may construct a second output or fuel-to-air ratio image 36 that displays a spatial distribution of fuel-to-air ratios within the flame. The system 20 provides the acquisition and reconstruction of high quality images from a single exposure using a single sensor array 24 that may be a CCD/CMOS sensor. The system is relatively low cost and more compact when compared to the traditional multi-camera, multispectral, imaging systems required to perform similar monitoring tasks. It is further contemplated that the placement of the multispectral mask 26 and the attenuation filter array 28 may be reversed with respect to one-another.

Figure 2:
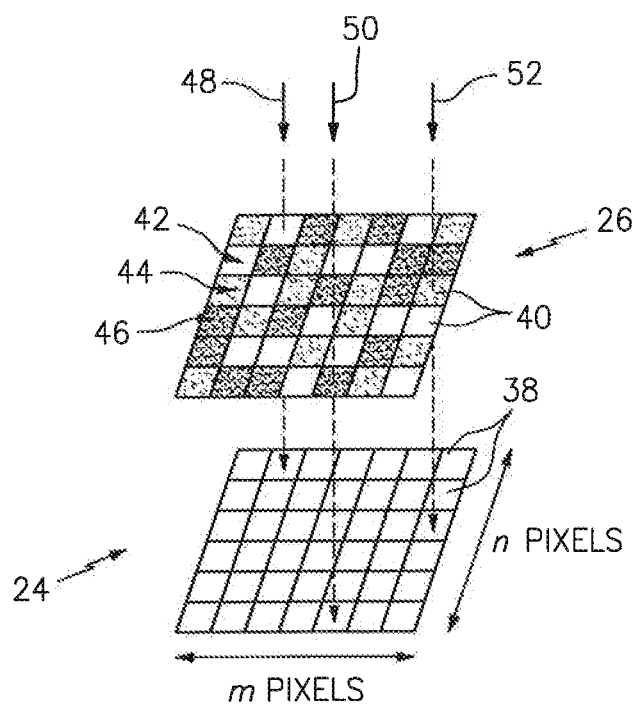
FIG. 2 is a perspective, exploded, view of a sensor array and multispectral mask array of the system.

Referring to FIGS. 1 and 2, the sensor array 24 may communicate with the computer 22 through a wired channel, or alternatively, may be any other optical, wireless, radio channel, or any other type of channel capable of transmitting images between two points including links involving the World Wide Web (www) or the internet. The sensor array 24 may be a focal plane array having a matrix or plurality of imaging, electronic, pixels 38. The multispectral mask array 26 is generally position in front of the sensor array 24 and has a plurality of cells 40 with each cell aligned to a corresponding pixel 38. The multispectral mask array 26 further has a plurality of band-pass filter types 42, 44, 46 (three illustrated) that are pseudo-randomly distributed amongst the cells 40 (i.e. each cell 40 has one of the three filter types 42, 44, 46). This pseudo-random order provides improved reconstructed images 34, 36 when used in conjunction with the algorithm 32 of the computer 22.

Figure 3:
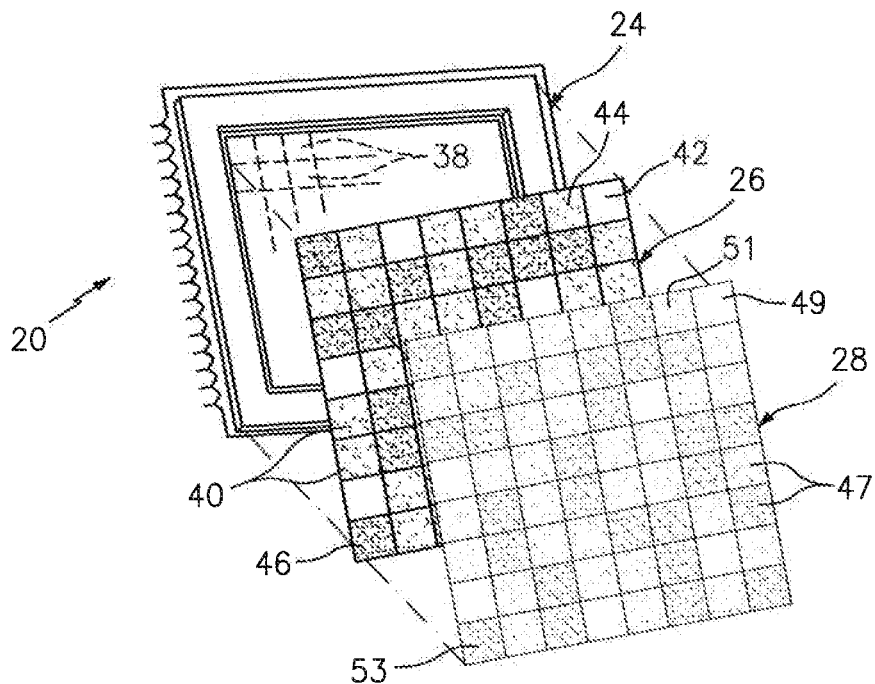
FIG. 3 is a perspective, exploded, view of the sensor and multispectral mask arrays with an attenuation filter array.

Referring to FIGS. 2 and 3, each filter type 42, 44, 46 is constructed to pass light emissions having wavelengths that fall within at least one specified wavelength range. Because the signal strength corresponding to one band-pass filter type may appreciably exceed the strength of another, the attenuation filter array 28 may be needed to prevent overexposure (or over saturation) at cells 40 passing high signal strengths, and where exposure time is held constant across the sensor array 24. Therefore, and like the mask array 26, the attenuation filter array 28 may have a plurality of cells 47 that generally align to each respective cell 40 of the multispectral mask array 26 and thus the pixels 38 of the sensor array 24. Generally, the attenuation capability at each cell 47 corresponds to the need of the respective cell 40 and may directly relate to the three filter types 42, 44, 46 (i.e. three degrees of attenuation). That is and as one example, the filter array 28 may have three attenuating types 49, 51, 53 corresponding to the respective filter types 42, 44, 46.

The multispectral mask array 26 and the attenuation filter array 28 may be fabricated on respective glass substrates with the multispectral mask array 26 located between the sensor array 24 and the attenuation filter array 28 (i.e. the mask array 26 is behind the filter array 28). Alternatively, each band-pass filter type 42, 44, 46 can be embedded directly upon the sensor array 24 (i.e. at the wafer level, respective pixel to respective cell). Similarly, each respective attenuation type 49, 51, 53 of each cell 47 can be embedded directly upon the sensor array 24 and/or multispectral mask array 26 at the wafer level. Alternatively, the attenuation filter array 28 may be thin attenuation films directly adhered to the glass substrate of the multispectral mask array 26 or adhered to the individual cells 40 at a wafer level.

Figure 4:
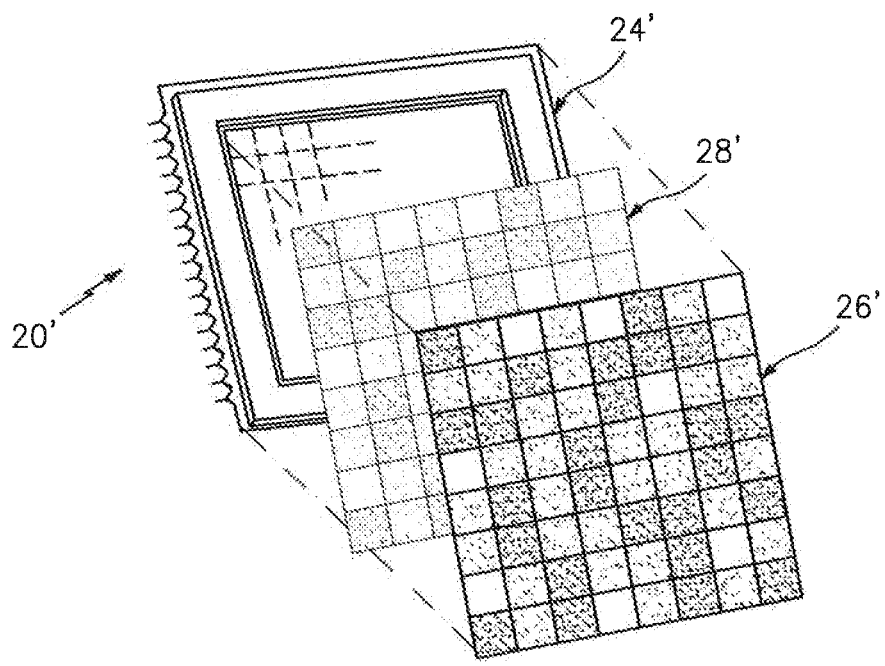
FIG. 4 is a perspective, exploded, view of a second embodiment of the arrays of the system.

Referring to FIG. 4, a second embodiment of the arrays is illustrated with like elements having like identifying numerals except with the addition of a prime symbol. In the second embodiment, an attenuation filter array 28' may be generally located behind a multispectral mask array 26'. That is the filter array 28' is located between the sensor array 24' and the mask array 26'. As previously described, construction of one or more of the arrays may be on a glass substrate or formed at the wafer level, or any variety of combination and orientations.

More specific to the turbine engine combustor flame application, it is known that the spatial distributions of fuel-to-air ratios and heat release in the reaction zone of a combustor are important for controlling the performance of combustion systems for fuel efficiency and reliability. The present disclosure provides a means to evaluate and monitor these properties through chemiluminescence imaging. More specifically, the heat release of the flame 30 can be measured utilizing an electronically excited methylidyne radical ($CH^*$) and a hydroxide radical ($OH^*$) of the flame 30. Further, the ratio of an electronically excited dicarbon radical over the methylidyne radical ($C2^*/CH^*$) is proportional to the fuel-to-air ratio in hydrocarbon-air flames.

Light emission from these radicals has known spectral properties. For example, wavelengths signifying the chemiluminescence presence of $C2^*$ may fall within a wavelength range of about 503 nm to 519 nm, and wavelengths signifying the chemiluminescence presence of $CH^*$ may fall within a wavelength range of about 422 nm to 432 nm. Yet further, background radiation due to an electronically energized carbon dioxide radical ($CO_2^*$) may have a broadband and thermal emission identified by three wavelength ranges of about 442 nm to 459 nm, 520 nm to 539 nm, and 600 nm to 617 nm. Band-pass filter type 42 may be applied to only pass light rays 48 signifying the presence of $C_2^*$, band-pass filter type 44 may be applied to only pass light rays 50 signifying the presence of $CH^*$, and band-pass filter 46 may be applied to only pass light rays 52 signifying the presence of $CO_2^*$. Because $CO_2^*$ is wide band (i.e. has three wavelength ranges), the band-pass filter 46 is a compound filter (i.e. each cell 40 associated with the band-pass filter 46 actually has three band-pass filters).

The light rays or emissions 48 50, 52 from the combustor flame 30 are filtered by the respective band-pass filter types 42, 44, 46 resulting in a patchwork image. As can be appreciated, the different intensities in the resulting images (not yet reconstructed) are irregularly spaced or geometrically unordered, corresponding to the spatial irregularity of mask array 26. The imaging reconstruction through use of the algorithm 32 depends on a mathematical property called sparsity. Sparsity is a property whereby some data (e.g. an image), may be represented by only a few non-zero numbers (also called coefficients) that multiply an appropriate set of basis functions. Natural imagery is known to be sparse because these images can be compressed (using relatively few coefficients and Fourier or Wavelet basis functions) and accurately reconstructed from these few coefficients.

Each wavelength range(s) of each band-pass filter type 42, 44, 46 corresponds to a respective spectral band. The non-reconstructed image of the flame 30 is captured through the mask array 26. The pixels 38 corresponding to one spectral band are called a pseudo-random image. For each exposure, then, there are several pseudo-random images each corresponding to the pixels of each spectral band (three images in the present example). From the acquired pseudo-random images, computational methods are used to reconstruct the desired multispectral images.

A mask of N discrete different spectral bands is created. There are, therefore, N pseudo-random images for any flame image 30 corresponding to the N spectral bands. The darkest pseudo-random image comprises the pixels through the darkest mask. Similarly, the next darkest pseudo-random image comprises the pixels through the next darkest mask, etc. For each exposure, then, there are N pseudo-random images each corresponding to the pixels 38 of one spectral band. For each pseudo-random image (corresponding to each spectral band), there are a limited number of observed pixels (1/N), from which to reconstruct the whole image. Each pixel 38 of the sensor array 24, comprising n-by-m pixels, is covered by an n-by-m size mask array 26 where each pixel of the sensor array 24 is covered by exactly one cell 40 of the mask array 26 and, therefore, one spectral band.

The method of generating a pseudo-random mask may vary. In one example, different spectral bands (e.g. colors) are assigned independently at each mask array cell 40 and uniformly throughout the mask array 26. In more general case, mask levels can be correlated and uniformly distributed on average. The magnitude of the spatial variation of mask levels in a subset of adjacent locations is the key parameter of a distribution that may control the statistical properties of the mask. This exemplary distribution depends on the number of mask array cells 40 in the subset and on a correlation function. Specifically, in the former case of the independently distributed mask levels, the squared magnitude of spatial variation may be directly proportional to the number of mask levels in the subset. In the latter case of correlated distributions this dependence can be modified. One of the most common examples is a power law dependence where the standard deviation is proportional to $N^\gamma$ where N is the number of mask levels in a subset and $\gamma$ is a parameter we choose. For image acquisition and image processing applications, the correlation, and therefore the parameter $\gamma$, can be optimized to reduce the local non-uniformity of the mask array 26 and thereby increase quality of image reconstruction.

The image reconstruction algorithm 32 may be a Dictionary Learning algorithm for image inpainting. The disclosure includes the following two steps:
1) Pseudo-random Image Acquisition: the traditional image sensor array 24 with the attached pseudo-random mask array 26 takes a single exposure acquiring a plurality of pseudo-random images.
2) Image Reconstruction: From the acquired pseudo-random images, there are two methods that may be used to reconstruct the desired multi-spectral image. One is a local patch based method (i.e., Dictionary Learning based image reconstruction). The other is a global image based method, i.e. $l_1$/TV, based image reconstruction. The Dictionary Learning based method is discussed in detail below.

The idea of Dictionary Learning is to learn a compact dictionary from the pseudo-random sampled image to reconstruct the high resolution images 34, 36. A dictionary (denoted as $\Phi$, also called a sampling matrix or a sensing matrix) for an image, x, allows accurate reconstruction provided that the following two conditions are satisfied:
1) Sparsity: The mathematical representation of the image, $\Phi x$, is sparse given an over-complete and redundant dictionary $\Phi$ (the redundancy here means that the number of dictionary atoms is much larger than the dimension of image patches of x, which implies that $\Phi x$ contains many zeros). As mentioned above, sparsity is a property whereby an image may be represented by only a few non-zero numbers (also called *coefficients*) which multiply an appropriate set of basis functions (each basis function is a vector called an atom, the collection of atoms form a dictionary as the dictionary's columns).
2) Incoherency: The sensing matrix/measurement matrix $\Phi^T$ has full spark. The spark of a dictionary (matrix) is the smallest number of columns that are linearly dependent. Full spark means that no square submatrix of the matrix $\Phi^T$ is singular. If columns are linearly dependent, then they will add no new information to the sampling process. The spark is of use in the theory of compressive sensing, where requirements on the spark of the measurement matrix $\Phi^T$ are used to ensure stability and consistency of the mathematical techniques. A related measure of the incoherency between dictionary atoms is the well-known Restricted Isometry Property (RIP).

The pseudo-randomness of the mask array 26 is important to ensure the incoherency of the sensing matrix $\Phi^T$. A regular grid mask will have linear dependencies between dictionary atoms such that $\Phi^T$ has non-full spark and has a worse RIP than for a pseudo-random mask. Dictionary Learning reconstruction results using a spatially regular grid mask are far worse than when using a pseudo-random mask.

The dictionary-learning-based image reconstruction uses image patches. First, a pseudo-random image is divided into a set of overlapping patches, $x_i$, each of size a×a (for example, a=8). (Hereafter the patch $x_i$ is considered to be a column vector as with the well-known Matlab command vect($x_i$).) The sparsity constraint is exploited in that each patch of the image is represented as a sparse combination of a set of dictionary atoms. Images can be reconstructed from an individual dictionary learned from each pseudo-random image, or from a single dictionary learned from all pseudo-random images. The learning of the dictionary is described as follows.

$$\min_{\alpha,\Phi} \sum_{i=1}^{n} \frac{1}{2}\|x_i - \Phi\alpha_i\|_2^2 \text{ such that } \|\alpha_i\|_0 \leq \tau_0$$

where $x_i$ are image patches, $\Phi$ is the dictionary, $\alpha_i$ are the sparse coefficients, and $\tau_0$ is the sparsity.

The intuitive interpretation of this optimization problem is that we are computing a dictionary $\Phi$ and coefficients $\alpha$ such that the sum of the differences between the image patches $x_i$ and their approximation from a dictionary, $\Phi_\alpha$, is small (each individual patch difference is the term $\|x_1-\Phi\alpha_i\|_2^2$ which measures how different the patch is from its sparse dictionary representation). The notation $\|\cdot\|_2^2$ is a difference measure, i.e. Euclidean distance (squared) between two vectors. The summation $$\sum_{i=1}^{n}$$

adds up all the individual patch differences. At the same time that we minimize the patch differences, we also want to ensure that the representation is sparse (this is the term $\|\alpha_i\|_0 \leq \tau_0$) which enforces that the sparsity of a is less than some small number $\tau_0$ that we specify.

Thus, solving this optimization problem finds a dictionary that can represent all the image patches where each patch representation only needs a few dictionary elements. The mathematical theory guarantees that if we compute this dictionary, we can reconstruct the entire image even if we only have 1/N of the actual pixel values. The dictionary learning proceeds as follows.

Initially, the dictionary, $\Phi$, may be set to any value or to the well known singular value decomposition (SVD) of all patches. The learning of a dictionary has two main steps:
1) Sparse coding step: For each patch $x_i$, compute a sparse representation, $\alpha_i$, using any pursuit algorithm (e.g., the well-known basis pursuit algorithm) such that each $x_i$ is a combination of a sparse set of the dictionary atoms.
2) Dictionary update step: Each atom of the dictionary $\Phi$ is updated as the first eigenvector of the error matrix from the sparsity fitting for the group of patches using this atom.

The two steps repeat until converged. This procedure is generally known in the art.

This disclosure advantageously exploits the pseudo-random distribution of spectral bands in the mask array 26. In particular, the disclosed image reconstruction is based on solving an optimization problem. A key requirement of this type of optimization problem is that the spatial (spatiotemporal) sampling is pseudo-random—specifically, it has the full spark or good RIP. The pseudo-randomness may come from any of a number of underlying pseudo-random number distributions. The pseudo-random mask array 26 can also be optimally designed to have a better spark or RIP property.

The term "pseudo-random" as used herein need not be truly pseudo-randomly generated. Specifically, the pseudo-random distribution may be truly random or may be approximately random as generated by any number of techniques such as spatial correlation optimized methods. However, the mask array 26 should not be regularly ordered.

The imaging system 20 may be generally used in a laboratory setting and toward the development of gas turbine engines and combustors thereof. Alternatively, the imaging system 20 may be an actual system of a combustor that monitors combustion performance and is capable of sending output signals to a combustor or engine controller that in-turn may act to change various engine operating parameters. One example of such an imaging system is disclosed in U.S. Pat. No. 8,432,440 and incorporated herein by reference.

Figure 5:
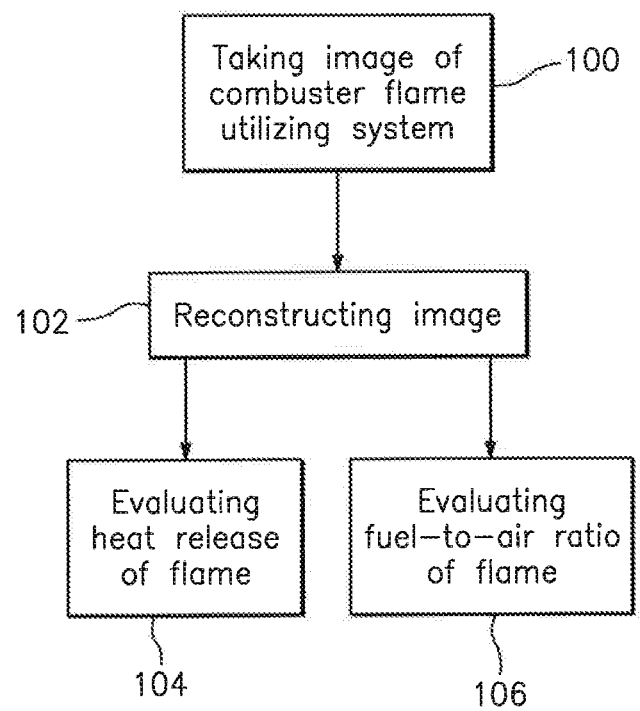
FIG. 5 is a flow chart of a method of monitoring a combustor flame utilizing the system.

Referring to FIG. 5 a method of monitoring the combustor flame 30 may be initiated through step 100 that includes taking an image of the flame 30 utilizing the system 20. As step 102, the image is reconstructed utilizing the reconstructing algorithm 32 of the computer 22. With the image reconstructed and as step 104, the spatial distribution of flame heat release may be evaluated through the production and review of the heat image 34. In addition and as step 106, the spatial distribution of fuel-to-air ratios may be evaluated through the production and review of the fuel-to-air ratio image 36.

It is understood that relative positional terms such as "forward," "aft," "upper," "lower," "above," "below," and the like are with reference to the normal operational attitude and should not be considered otherwise limiting. It is also understood that like reference numerals identify corresponding or similar elements throughout the several drawings. It should be understood that although a particular component arrangement is disclosed in the illustrated embodiment, other arrangements will also benefit. Although particular step sequences may be shown, described, and claimed, it is understood that steps may be performed in any order, separated or combined unless otherwise indicated and will still benefit from the present disclosure.

The foregoing description is exemplary rather than defined by the limitations described. Various non-limiting embodiments are disclosed; however, one of ordinary skill in the art would recognize that various modifications and variations in light of the above teachings will fall within the scope of the appended claims. It is therefore understood that within the scope of the appended claims, the disclosure may be practiced other than as specifically described. For this reason, the appended claims should be studied to determine true scope and content.

What is claimed:

1. A chemiluminescence imaging system comprising:
a sensor array including a plurality of pixels operable to capture a plurality of pseudo-random images;
a multispectral mask array having a first plurality of cells with each cell of the first plurality of cells associated with a respective pixel and being one of a plurality of band-pass filter types with the plurality of band-pass filter types being randomly distributed across the multispectral mask, where each of the band-pass filter types is associated with a respective pseudo-random image included in the plurality of pseudo-random images;
an attenuation filter array adjacent to the multispectral mask array and having a second plurality of cells with each cell of the second plurality of cells associated with a respective cell of the first plurality of cells of the multispectral mask array for obtaining proper exposure of each of the plurality of pixels; and
a computer having an image reconstruction algorithm, wherein each of the pseudo-random images is based on less than an entirety of the plurality of pixels such that each pseudo-random image is sparse, wherein the algorithm is operable to construct a plurality of whole images based on the plurality of pseudo-random images, wherein each of the whole images corresponds to a respective one of the plurality of pseudo-random images, and wherein each of the whole images corresponds to the entirety of the plurality of pixels.

2. The chemiluminescence imaging system set forth in claim 1, wherein the sensor array is a charge coupled device.

3. The chemiluminescence imaging system set forth in claim 1, wherein the system has only one sensor array that is part of a camera.

4. The chemiluminescence imaging system set forth in claim 1, wherein each one of the plurality of band-pass filter types are configured to measure a distinct wavelength range of spectral light of a turbine combustor flame.

5. The chemiluminescence imaging system set forth in claim 4, wherein a first band-pass filter type of the plurality of band-pass filter types passes light emissions within a wavelength range of about 503 nm to 519 nm associated with an electronically excited dicarbon radical, and a second band-pass filter type passes light emissions within a wavelength range of about 422 nm to 432 nm associated with an electronically excited methylidyne radical.

6. The chemiluminescence imaging system set forth in claim 5, wherein a third band-pass filter is a wide-band filter and passes light emissions within wavelength ranges of about 442 nm to 459 nm, 520 nm to 539 nm, and 600 nm to 617 nm.

7. The chemiluminescence imaging system set forth in claim 6, wherein the system has only one sensor array that is part of a camera.

8. The chemiluminescence imaging system set forth in claim 1, wherein the attenuation filter array is a plurality of films adhered to the multispectral mask array.

9. The chemiluminescence imaging system set forth in claim 1, wherein the attenuation filter array is orientated behind the multispectral mask array.

10. The chemiluminescence imaging system set forth in claim 1, wherein the attenuation filter array is orientated in front of the multispectral mask array.

11. The chemiluminescence imaging system set forth in claim 1, wherein the sensor array is a CMOS.

12. The chemiluminescence imaging system set forth in claim 1, wherein a first image of the whole images corresponds to a spatial distribution of heal release from a flame, and wherein a second image of the whole images corresponds to a spatial distribution of fuel-to-air ratios within the flame.

13. The chemiluminescence imaging system set forth in claim 1, wherein the sensor array is operable to capture the plurality of pseudo-random images during a single exposure.

* * * * *